United States Patent [19]
Chudzik et al.

[11] Patent Number: 5,707,818
[45] Date of Patent: *Jan. 13, 1998

[54] DEVICE AND METHOD FOR SIMULTANEOUSLY PERFORMING MULTIPLE COMPETITIVE IMMUNOASSAYS

[75] Inventors: Stephen J. Chudzik; Martha J. Hamilton, both of St. Paul, Minn.

[73] Assignee: BSI Corporation, Eden Prairie, Minn.

[*] Notice: The term of this patent shall not extend beyond the expiration date of Pat. No. 5,541,075.

[21] Appl. No.: 354,953

[22] Filed: Dec. 13, 1994

[51] Int. Cl.[6] .................... G01N 33/53; G01N 33/558
[52] U.S. Cl. .................. 435/7.93; 422/55; 422/56; 422/57; 422/58; 422/61; 435/7.92; 435/287.1; 435/287.2; 435/287.7; 435/810; 435/970; 435/973; 436/164; 436/169; 436/514; 436/518; 436/524; 436/528; 436/530; 436/805; 436/810; 436/815; 436/816; 436/901
[58] Field of Search ................ 422/55, 56, 57, 422/58, 61; 435/7.92, 7.93, 810, 970, 973, 287.1, 287.2, 287.7; 436/514, 518, 524, 528, 530, 164, 169, 805, 810, 815, 816, 901

[56] References Cited

U.S. PATENT DOCUMENTS

| | | | |
|---|---|---|---|
| 4,270,920 | 6/1981 | Kondo et al. | 435/22 |
| 4,275,149 | 6/1981 | Litman et al. | 435/7.91 |
| 4,299,916 | 11/1981 | Litman et al. | 435/805 |
| 4,959,307 | 9/1990 | Olson | 422/56 |
| 4,963,468 | 10/1990 | Olson | 422/56 |
| 5,085,987 | 2/1992 | Olson | 422/56 |
| 5,085,988 | 2/1992 | Olson | 422/56 |
| 5,238,652 | 8/1993 | Sun et al. | 422/61 |
| 5,252,496 | 10/1993 | Kang et al. | 436/529 |
| 5,424,220 | 6/1995 | Goerlach-Graw et al. | 436/568 |

FOREIGN PATENT DOCUMENTS 2239313  6/1991  United Kingdom.

OTHER PUBLICATIONS

Buechler, et al, "Stimultaneous Detection of Seven Drugs of Abuse by the Triage Panel for Drugs of Abuse," *Clin. Chem.* 38(9):1678–1684 (1992).

*Primary Examiner*—Christopher L. Chin
*Attorney, Agent, or Firm*—Fredrikson & Byron, P.A.

[57] ABSTRACT

A device and related method for simultaneously performing a plurality of immunoassays to detect the presence of respective analytes in a sample. The device involves the use of a unitary bibulous material providing one or more flow paths having a common origin site and a plurality of respective reagent zones providing the reagents necessary for performing a visual read-out, competitive immunoassay for the presence of the respective analyte.

11 Claims, 1 Drawing Sheet

DEVICE AND METHOD FOR SIMULTANEOUSLY PERFORMING MULTIPLE COMPETITIVE IMMUNOASSAYS

TECHNICAL FIELD

The present invention relates to the field of diagnostic immunoassays and related devices for carrying out such assays. In another aspect, the invention relates to assays for analytes such as drugs of abuse or their metabolites. In another aspect, the invention relates to devices or means for simultaneously carrying out multiple assays for different analytes within a single sample.

BACKGROUND OF THE INVENTION

The use of analytical assays, including those used to determine the presence of drugs of abuse, has grown rapidly over the past decade. By 1993, the U.S. drug-testing market, alone, was estimated to be at least $500M. The drug-testing industry is poised for further growth as a result of new federal U.S. regulations that will significantly increase the number of workers subject to testing for drug and alcohol abuse.

At present, most drug testing involves sample collection followed by instrument-based "wet chemistry" laboratory analysis. However, the on-site, or "point of care" market has been growing rapidly over the past two years. Although no current figures are available, the market for non-instrumented immunoassay-based drugs of abuse test kits appears to be growing at the rate of 20–40% per year.

Currently, there are a number of single analyte immunoassay-based drugs of abuse diagnostic tests on the market. These include tests produced by Roche Diagnostic Systems, Hansen Hong Biomedical Co. Ltd., Drug Screening Systems, Editek, Inc., Hycor Biomedical, U.S. Drug Testing Inc., Thermedics Detection, Inc., and Fingerprint Biotek. Such devices generally work well for situations in which a specific drug is suspected. In many cases, however, such as in emergency room settings, a panel of tests are needed to quickly determine the drug or drugs that may be present in a given patient.

A variety of assay kits have been described having the capability to perform diagnostic assays. For instance, a series of patents issued to Olson (U.S. Pat. Nos. 4,959,307; 4,963,468; 5,085,987; and 5,085,988) relate to an immunoseparating strip having a bibulous material, a non-diffusively bound first receptor, and a non-diffusively bound second receptor. In each embodiment, however, the method of using the device requires the first step of preparing a test solution containing the sample, antibody for the analyte, and a conjugate of analyte and a label.

Others have disclosed the use of kits capable of performing two or more assays, including multi-analyte on-site formats. A kit available from Biosite ("Triage" brand), is said to allow the differential detection of the presence of several common drugs of abuse in a single urine or serum sample. See, for example, Buechler, et al, *Clin. Chem.* 38(9):1678–1684 (1992). At least one drawback of this device is the need to separately add sample to a region containing lyophilized reagents, where it is left for a period of time (e.g, 10 minutes), in order to allow the sample to reconstitute and equilibrate with the reagents.

This and other multi-analyte test kits currently on the market have several drawbacks. Present formats tend to be quite complex, with specific affinity constants playing a key role in the competitive binding reactions. Moreover, the formats can suffer from false results if the patient is on high doses of the analyte drug. Also, present formats typically require exact reagent concentrations (i.e., ratios of analyte to anti-analyte), which can be compromised if one of the ligand-receptor pair begins to deteriorate.

Particularly troublesome are kits that rely on the use of an immobilized antibody or binding reagent, where the amount of this reagent needs to be rigidly controlled. The binding capacity of immobilized receptors can be highly dependent on the particular immobilization methods and conditions. This dependence causes the manufacture of such assays to be unpredictable and difficult to reproduce. Shelf life stability can be affected as well.

What is clearly needed is a multiple analyte test kit useful for a number of different drugs of abuse, that is easier to manufacture and simple and reliable in use.

SUMMARY OF THE INVENTION

Figure 1:
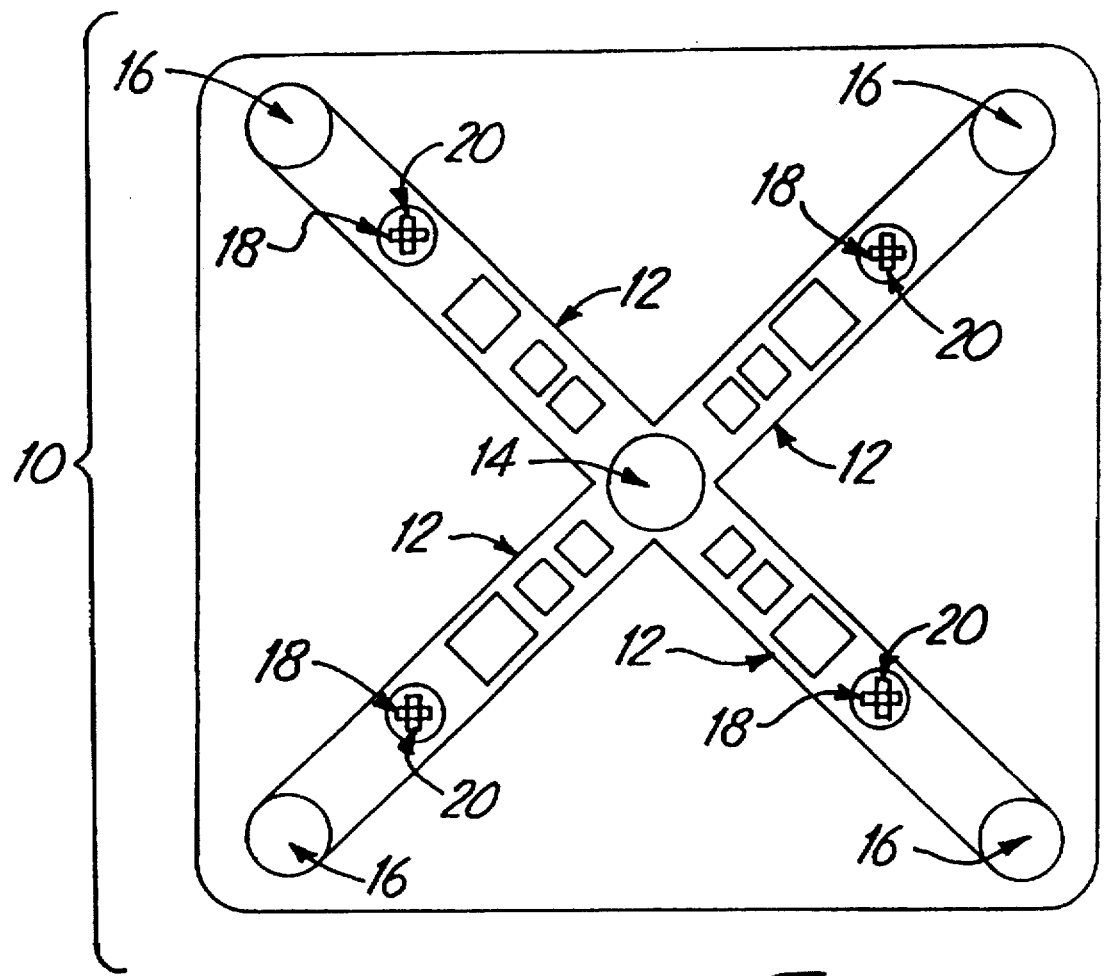
FIG. 1 depicts a diagram of a preferred embodiment of the present invention, having a multiple analyte, immunoassay-based on-site test format.
Figure 1:
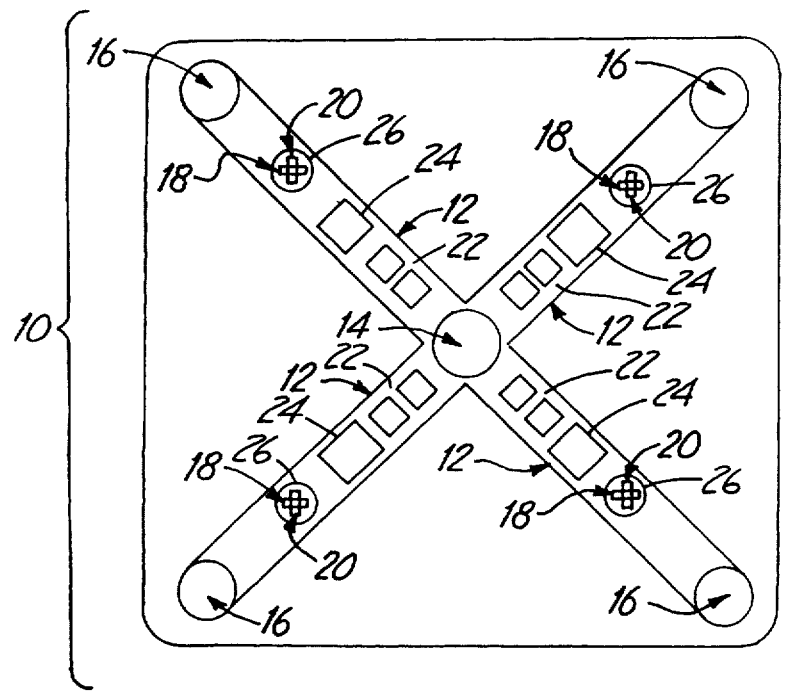

The present invention provides a device and related method for simultaneously performing a plurality of immunoassays to detect the presence of respective analytes in a sample, the device comprising a unitary bibulous material providing one or more flow paths, each flow path comprising:

(a) a common origin site on the bibulous material for the simultaneous application of a fluid sample, (b) a plurality of respective reagent zones downstream from the origin, the reagent zones of each immunoassay providing the reagents necessary for performing a visual read-out, competitive immunoassay for the presence of the respective analyte, the zones comprising, in order and in the direction of flow:

(i) a competition zone comprising a detectable analyte-conjugate and first binding partner for the analyte, both being diffusively positioned in such a manner that any free analyte present in the sample is capable of binding to the first binding partner in a competitive manner with the analyte-conjugate;

(ii) a retention zone comprising an excess mount of a second, nondiffusively bound reagent capable of binding to free or bound first binding partner in order to remove it from continued flow in the flow path; and (iii) a read out zone comprising nondiffusively bound receptor capable of binding to analyte-conjugate, but not to unconjugated analyte, in a detectable manner.

The flow paths preferably further each comprise one or more positive and/or negative procedural control zones and reagents. In one preferred embodiment, the device further comprises a terminal site downstream from the sequential reagent zones and comprising an indicator reagent for confirming the completion of the respective assay.

In a particularly preferred embodiment, the device comprises an inert holder comprising top and bottom portions for supporting the bibulous material, the top portion providing an opening for fluid sample access to the common origin, as well as openings for viewing the respective read-out and terminal indicator sites along each flow path.

In the course of using a device as described above, the presence of increasing amounts of free analyte in a sample leads to the binding of less analyte-conjugate to the first binding partner. In turn, an increased amount of free analyte-conjugate is able to continue down the flow path. Ultimately, the free analyte-conjugate becomes non-diffusively bound to a corresponding binding partner in the read-out zone, and is there detected in order to provide a positive indication of the presence of analyte in the original sample.

In one embodiment, the flow paths for each assay can be provided in an overlapping and/or side-by-side manner, and in the same direction along the bibulous material. In a preferred embodiment, the device provides a separate, discrete flow path for each analyte, the flow paths being positioned to extend in a radial direction from the common origin.

In a particularly preferred embodiment, the present invention provides a multi-analyte assay capable of differentially detecting the presence of one to four drug(s) in a single sample of urine or serum. Such analytes include THC, cocaine, opiates, and amphetamines, which are detected without interference from the other analytes.

DETAILED DESCRIPTION

In the present specification, the following words and phrases will have the meaning ascribed to them:

"zone" will refer to a discrete situs containing one or more reagents and positioned along the flow path of a particular assay, each zone or situs having a surface area less than that of the bibulous material;

"downstream", as applied to zones, will refer to a zone that is flowably separated from the preceding zone, and in the direction of flow of a sample. In a typical embodiment, for instance, each zone will be on the order of one or more millimeters from each other. Additionally, there may be two or more discrete regions within zones, such as the regions carrying analyte-conjugate and fast binding partner, respectively in the competition zone. Alternatively, with non-interfering reagents, zones and/or regions within zones may occasionally be positioned in an overlapping configuration with preceding and/or following zones.

"unitary", as applied to the bibulous material, means that when a single aqueous sample is added to the origin, the sample is capable of flowing along each flow path.

"simultaneous" will mean that each of the assays on a single device are capable of being performed at substantially the same time and by the application of a single sample to the origin.

"competitive" will mean that the amount of analyte-conjugate that becomes bound to free first binding partner is dependent upon and related to the presence or absence of analyte in the sample.

The present invention provides a device for simultaneously performing a plurality of immunoassays to detect the presence of respective analytes in a sample. Correspondingly, the device and method of the present invention can be used for the analysis or detection of one or more suitable analytes. Suitable analytes include those capable of being provided in the form of a conjugate. Alternatively, the analyte can be in the form of a derivative or metabolite of the compound of interest.

Generally, an analyte is any compound to be detected that is capable of being bound by a receptor, and capable of being recovered in synthetic and/or purified form sufficient to allow it to be conjugated and used in a competitive assay with sample analyte and the receptor. These compounds include mono-epitopic analytes of relatively small molecular weight (e.g., about 100 to 2000), and poly-epitopic antigens of larger molecular weight (e.g., greater than about 2000). Representative analytes are those described, for instance, in U.S. Pat. Nos. 4,299,916 and 4,275,149, the disclosures of both of which are incorporated herein by reference.

Examples of suitable analytes include, but are not limited to, pesticides and their metabolites and derivatives (e.g., polyhalogenated biphenyls, phosphate esters, thiophosphates, carbamates, polyhalogenated sulfenamides), and drugs and their metabolites and derivatives (e.g., alkaloids, steroids, lactams, aminoalkylbenzenes, benzheterocyclics, purines, vitamins, antibiotics, nucleosides and nucleotides, drugs derived from marijuana, and miscellaneous drugs).

The device and method of the present invention can be used with any suitable sample. Generally, and preferably, the sample is an aqueous one that is obtained directly from the source (e.g., urine or blood). Alternatively, the sample can be prepared by mixing or extracting a non-aqueous sample (e.g., tissue) with an aqueous solvent (e.g., buffered solution). Generally, the sample is any substance suspected of containing the compound or compounds of interest. This includes the analysis of ground water for contaminants, the analysis of agricultural products for naturally occurring toxic agents such as aflatoxin, and the like.

Occasionally, analyses of this type will require an extraction step in which a sample is mixed with a liquid extraction media which can be aqueous, organic, or an aqueous/organic mixture. Upon extraction of the material of interest, the extracting solution itself can be used as the sample and can be evaluated directly or concentrated, diluted, evaporated, and reconstituted, etc. before evaluation in the instant device.

Additional examples of evaluations requiting extraction include pesticide residues, bacterial metabolites or other contaminants in meat or seafood, and herbicide residues or other pollutants in soil samples.

A device of this invention comprises a unitary bibulous material providing one or more flow paths., Preferably, although not necessarily, the bibulous material will actually be provided in the form of a single, integral material. Alternatively, the bibulous could be unitary by the overlapping of discrete materials at or near the origin. Examples of suitable bibulous materials include (nitrocellulose membranes, nylon membranes, or other commercially available membranes).

Bibulous materials useful in the instant device include porous materials that are susceptible to being traversed by an aqueous medium in response to capillary force. Such materials are generally hydrophilic or are capable of being rendered hydrophilic and include inorganic powders, such as silica and alumina; natural polymeric materials particularly cellulosic materials such as filter paper, chromatographic paper and the like; synthetic or modified naturally occurring polymers such as nitrocellulose, cellulose acetate, poly (vinyl chloride), polyacrylamide, crosslinked dextran, agarose, etc.; either used alone or in conjunction with other materials. A preferred bibulous material includes glass fiber filter paper. The bibulous material can be attached to a support, or may provide its own support. The bibulous material may contain functional groups, or be capable of being functionalized to permit covalent bonding or receptors to other moieties.

Each flow path in a device of the present invention comprises a common origin site on the bibulous material for the simultaneous application of a fluid sample. As can be seen, the origin is "common" in that the application of a single sample serves to begin the flow of sample simultaneously in each flow path.

Each flow path in a device of the present invention further comprises a plurality of respective reagent zones downstream from the origin. The reagent zones of each immunoassay provide the reagents necessary for performing a visual read-out, competitive immunoassay for the presence of the respective analyte. In a preferred embodiment, the reagent zones provide each of the reagents necessary, i.e., without the need for wet chemistry steps or the need to physically move or apply reagents along the path or in the course of the assay.

The zones of a particular flow path comprise, in the order and direction of flow, a competition zone comprising analyte-conjugate and first binding partner for the analyte, both being diffusively positioned in such a manner that any free analyte present in the sample is capable of binding to the first binding partner in a competitive manner with the analyte conjugate. The first binding partner is a receptor for the analyte.

A receptor is any compound or composition capable of recognizing a particular spatial and polar organization of the analyte of interest. Illustrative receptors include naturally occurring receptors; e.g., antibodies, enzymes, lectins, and the like. A preferred receptor for the analyte is an antibody to the analyte. An antibody is an immunoglobulin or derivative or fragment thereof having an area on the surface or in a cavity which specifically binds to and is thereby defined as complimentary with a particular spatial and polar organization of another molecule. The antibody can be monoclonal or polyclonal, and can be prepared by techniques that are well known in the art, such as immunization of a host and collection or sera or hybrid cell line technology.

The analyte-conjugate is generally provided in the form of a label or tracer, for example a catalyst, usually an enzyme, conjugated to the analyte. A label can be any molecule or system of molecules bound or conjugated to the analyte that is capable of producing a perceptible signal. A preferred label consists of colloidal metal particles, or sol particles that are colored. Those skilled in the art will recognize that many elements are capable of functioning as a label, including, without limitation, radionuclides, fluorescent species, phosphorescent species, chemiluminescent materials, dyes, enzymes, sol particles, colored polymeric materials, and the like. Based upon the known binding kinetics of the monoclonal anti-drug antibodies, standard techniques can be used to prepare drug conjugates having the correct epitope available for antibody binding.

A flow path further comprises a retention zone comprising an excess amount of a second, non-diffusively bound reagent capable of binding to free or bound first binding partner in order to remove it from continued flow in the flow path. This first bound reagent is a receptor capable of binding to the first binding partner. A preferred first bound reagent is an antibody capable of binding to the first binding partner.

Since the first binding partner is preferably an antibody to the analyte, the first bound reagent is preferentially an antibody capable of binding to the antibody for the analyte. It can be, for example, an antibody raised in a different species than that used to raise the antibody for the analyte. The first bound reagent can also be a receptor, such as protein A, which binds to a particular site on the immunoglobulin molecule. In another embodiment, the first binding partner can be coupled to a molecule, such as biotin, and the first bound reagent can be specific for such a molecule, for example, antibiotin or avidin.

The approach of the present invention provides a particular advantage over many conventional assays employing immobilized receptors. As described above, the binding capacity of such immobilized receptors can be dependent upon the immobilization methods and conditions, such that the manufacture of such assays is unpredictable and difficult to reproduce. In the present invention, all immobilized receptor activity can be present in excess, thus permitting the development of an assay with predictable performance characteristics.

Lastly, a flow path further comprises a read out zone comprising nondiffusively bound receptor capable of binding to analyte-conjugate but not to unconjugated analyte in a detectable manner.

The second bound reagent is a receptor capable of binding to the analyte-conjugate, but not to the analyte alone. This receptor binds then, either to the label portion of the conjugate, or to an additional moiety provided by the conjugate (e.g., by virtue of the binding of analyte and label) but absent from the analyte alone. A preferred second bound reagent is an antibody capable of binding to the spacer moiety that is used to conjugate the analyte to the label.

In a particularly preferred embodiment, the read-out is provided in the form of the completion of a plus ("+") sign indicating the presence of analyte. In such an embodiment, the minus ("−") portion of the read-out can be provided by any suitable means.

In one embodiment, the minus portion is provided by the use of additional reagents positioned along the flow path. For instance, a detectable conjugate is positioned along the flow path, and preferably at the origin itself. The minus portion of the readout can be provided in the form of a non-diffusively bound antibody to the detectable conjugate. For example, when a conjugate of gold-KLH is present in diffusive form, with a non-diffusively bound anti-KLH antibody forming the minus portion of the readout zone.

Lastly, the flow path preferably further comprises a terminal site downstream from the sequential reagent zones and comprising an indicator reagent for confirming the completion of the respective assay. The indicator reagent is typically a material that is sensitive to the presence of the sample. It is generally a material that will change color in response to the presence of some moiety in the sample solution. Examples of such a reagent include pH indicator dyes, dyes sensitive to the presence of proteins, and dyes sensitive to hydration states.

The device of the present invention can be of any suitable form and dimensions in order to achieve the desired purpose. In a preferred embodiment, the device is provided in the form of an inert holder comprising top and bottom portions for supporting the bibulous material, the top portion providing an opening for fluid sample access to the common origin, as well as openings for viewing the respective read-out and terminal indicator sites along each flow path.

The manufacture of a typical design of the present test format will be described with reference to FIG. 1 of the Drawing. To the user, the test would appear as a single test device 10 having paths 12 that migrate and read out in each of four directions. Paths 12 each comprise a competition zone 22 (as shown, having discrete regions therein for analyte-conjugate and first binding partner, respectively), retention zone 24 and readout zone 26. The sample is added to the center well 14, and the test would be complete when the four completion indicator windows 16 change color. If the assay is operating properly, the negative portion 18 of the sign appears as a color change for each of the analytes. If the patient is drug positive for any of the analytes, then the respective plus portion of the readout sign 20 will appear as well.

A device as shown in FIG. 1 can be prepared and used in the following manner.

Gold-KLH. Keyhole limpit hemocyanin ("KLH") and colloidal gold are obtained from a variety of commercial sources, and conjugated according to standard methods.

Gold-ovalbumin-drugs. Ovalbumin is obtained from a commercial source and coupled to the desired analyte as well as to colloidal gold. Labeling of the carrier protein with colloidal gold is performed by standard methods. Reaction conditions are monitored in order to ensure that the colloidal gold does not interfere with the binding reaction of drug hapten to anti-drug antibody. Similar chemical methods are used for preparing conjugates for THC (marijuana), benzoylecgonine (cocaine), opiates (morphine, morphine glucuronide), amphetamine (amphetamine and methamphetamine).

Non-diffusively bound reagents. Reagents can be immobilized to the bibulous material via any suitable technique as will be apparent to those skilled in the art. Direct attachment methods include non-diffusive adsorption, non-diffusive absorption, attachment to microparticles that are themselves entrapped in the appropriate position, and covalent binding, such as by use of cyanogen bromide, carbonyl diimidazole, or glutaraldehyde. "Non-diffusive", as used in this respect, means that the reagent is sufficiently stable in its position under the conditions of the assay.

Diffusively positioned reagents. Conventional methods are employed for impregnating substrates such as paper with dry chemistry biomolecules. These methods are useful for: 1) optimizing substrate capacity; 2) optimizing the wettability of dried reagents; and 3) increasing the stability of dried reagents.

Indicator Strip. Conventional methods are employed for the preparation of a terminal indicator, for instance, by the use of a pH indicator that will change color when urine is present.

In one embodiment of the device, the diffusively positioned reagents are applied to the competition zone in the appropriate concentrations such that a visibly perceptible signal generated in the read-out zone only when the sample applied to the origin site contains analyte at or above a pre-determined concentration. When multiple analytes are being detected from the same sample this pre-determined concentration can be different for each analyte.

The operation of the device can be evaluated, for instance, by preparing spiked single drug samples in buffers, using varying concentrations of each drug. Limited cross-reactivity should be tested against other abused substances as well as various common prescription drugs. Spiked multi-drug samples are also tested, with particular emphasis on signal generation and possible signal interference. Signal generation can be "scored" visually against a standard color chart.

In one embodiment, normal human urine is spiked with varying doses of the four drugs of abuse. A total of five sources are used. Evaluation includes comparison of: 1) visually scored signal generation; 2) time for test completion; and 3) the presence of nonspecific binding.

The method of the present invention comprises the steps of providing a device of the type described above and using the device in the following manner:

(a) applying an aqueous sample to the unitary bibulous material at a common origin site of one or more flow paths, (b) allowing the sample to simultaneously flow through each flow path and sequentially through a plurality of respective reagent zones providing the reagents necessary for performing a visual read-out, competitive immunoassay for the presence of the respective analyte, the zones comprising, in order and in the direction of flow:

a competition zone comprising a detectable analyte-conjugate and first binding partner for the analyte, both being diffusively positioned in such a manner that any free analyte present in the sample is capable of binding to the first binding partner in a competitive manner with the analyte conjugate;

a retention zone comprising an excess amount of a second, non-diffusively bound reagent capable of binding to free or bound first binding partner in order to remove it from continued flow in the flow path; and a read out zone comprising nondiffusively bound receptor capable of binding to analyte-conjugate but not to unconjugated analyte in a detectable manner;

(c) allowing the sample to flow through a terminal site downstream from the sequential reagent zones and comprising an indicator reagent for confirming the completion of the respective assay, (d) determining the presence of each analyte in the sample by detecting the presence of the respective analyte-conjugate in each read-out zone, and assessing the positive and negative controls in each flow path in order to determine the proper performance of the respective assay.

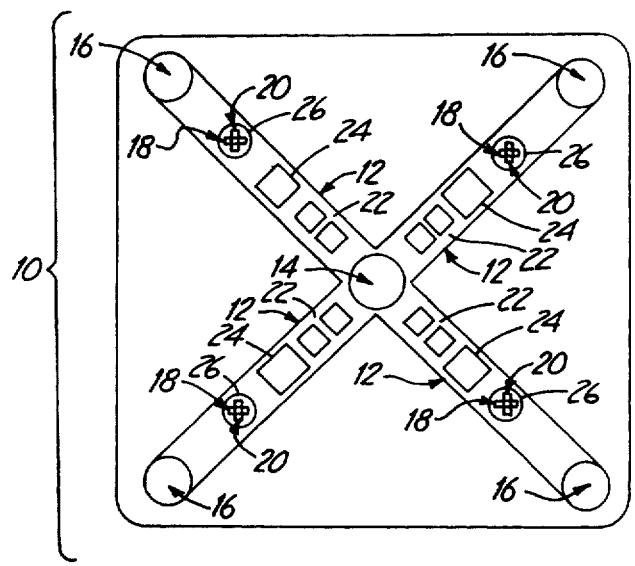

What is claimed is:

1. A device for simultaneously performing a plurality of competitive immunoassays to provide a positive readout for the presence of respective monoepitopic analytes in a sample, the device comprising a unitary bibulous material providing one or more flow paths, each flow path comprising:

(a) a common origin site on the bibulous material for the simultaneous application of a fluid sample, (b) a plurality of respective reagent zones downstream from the origin site, the reagent zones of each immunoassay providing the reagents necessary for performing a visual read-out, competitive immunoassay for the presence of the respective analyte, the zones comprising, in order and in the direction of flow:

(i) a competition zone comprising a detectable analyte-conjugate composed of analyte and label, and a first binding partner for the analyte, both being diffusively positioned in such a manner that any free analyte present in the sample is capable of binding to the first binding partner in a competitive manner with the analyte conjugate;

(ii) a retention zone comprising an excess amount of a second, nondiffusively bound reagent capable of binding to free or bound first binding partner in order to remove it from continued flow in the flow path; and (iii) a read out zone comprising nondiffusively bound receptor capable of binding in a detectable manner to the analyte-conjugate but not capable of binding to unconjugated analyte.

2. A device according to claim 1 further comprising, along the flow path, one or more positive and/or negative procedural control zones and reagents.

3. A device according to claim 2 wherein the positive control zone comprises a terminal site downstream from the sequential reagent zones and comprising an indicator reagent for confirming the completion of the respective assay.

4. A device according to claim 1 further comprising an inert holder comprising top and bottom portions for supporting the bibulous material, the top portion providing an opening for fluid sample access to the common origin, as well as openings for viewing the respective read-out and terminal indicator sites along each flow path.

5. A device according to claim 1 wherein the device provides a separate, discrete flow path for each analyte, the flow paths being positioned to extend in a radial direction from the common origin.

6. A device according to claim 5 wherein the device is capable of differentially detecting the presence of one to four drug(s) in a single sample of urine or serum.

7. A device according to claim 6 wherein the analytes are selected from the group consisting of tetrahydrocannabinol, cocaine, opiates, and amphetamines.

8. A device according to claim 1 wherein a spacer moiety is used to conjugate the analyte to the label, and the nondiffusively bound receptor is capable of binding to the spacer moiety.

9. A device according to claim 8 wherein the label comprises a colloidal metal particle.

10. A method for simultaneously performing a plurality of competitive immunoassays to detect the presence of respective monoepitopic analytes in a sample, the method comprising the steps of providing a device according to claim 1 and using the device in the following manner:

(a) applying an aqueous sample to the unitary bibulous material at a common origin site of one or more flow paths, (b) allowing the sample to simultaneously flow through each flow path and sequentially through a plurality of respective reagent zones providing the reagents necessary for performing a visual read-out, competitive immunoassay to provide a positive readout for the presence of the respective analyte, the zones comprising, in order and in the direction of flow:

a competition zone comprising a detectable analyte-conjugate and first binding partner for the analyte, both being diffusively positioned in such a manner that any free analyte present in the sample is capable of binding to the first binding partner in a competitive manner with the analyte conjugate;

a retention zone comprising an excess amount of a second, non-diffusively bound reagent capable of binding to free or bound first binding partner in order to remove it from continued flow in the flow path; and a read out zone comprising nondiffusively bound receptor capable of binding in a detectable manner to analyte-conjugate but not capable of binding to unconjugated analyte.

11. A method according to claim 10 wherein the method is capable of simultaneously performing a plurality of immunoassays to detect the presence of respective analytes in a sample, wherein the presence of increasing amounts of free analyte in a sample leads to the binding of less analyte-conjugate to the first binding partner.

* * * * *

UNITED STATES PATENT AND TRADEMARK OFFICE
CERTIFICATE OF CORRECTION

PATENT NO. : 5,707,818  
DATED : January 13, 1998  
INVENTOR(S) : Stephen J. Chudzik, et al.

Page 1 of 3

It is certified that error appears in the above-identified patent and that said Letters Patent is hereby corrected as shown below:

The title page, showing an illustrative figure, should be deleted and substitute therefor the attached title page.

Delete Drawing Sheet 1, and substitute therefor the Drawing Sheet consisting of FIG. 1, as shown on the attached page.

On the title page, delete --[*] Notice: The term of this patent shall not extend beyond the expiration date of Pat. No. 5,541,075.--.

Signed and Sealed this

Twenty-third Day of June, 1998

Attest:

BRUCE LEHMAN

*Attesting Officer*   *Commissioner of Patents and Trademarks*

United States Patent [19]

Chudzik et al.

[11] Patent Number: 5,707,818
[45] Date of Patent: *Jan. 13, 1998

[54] DEVICE AND METHOD FOR SIMULTANEOUSLY PERFORMING MULTIPLE COMPETITIVE IMMUNOASSAYS

[75] Inventors: Stephen J. Chudzik; Martha J. Hamilton, both of St. Paul, Minn.

[73] Assignee: BSI Corporation, Eden Prairie, Minn.

[*] Notice: The term of this patent shall not extend beyond the expiration date of Pat. No. 5,541,075.

[21] Appl. No.: 354,953

[22] Filed: Dec. 13, 1994

[51] Int. Cl.[6] .................... G01N 33/53; G01N 33/558
[52] U.S. Cl. ................... 435/7.93; 422/55; 422/56; 422/57; 422/58; 422/61; 435/7.92; 435/287.1; 435/287.2; 435/287.7; 435/810; 435/970; 435/973; 436/164; 436/169; 436/514; 436/518; 436/524; 436/528; 436/530; 436/805; 436/810; 436/815; 436/816; 436/901
[58] Field of Search ................... 422/55, 56, 57, 422/58, 61; 435/7.92, 7.93, 810, 970, 973, 287.1, 287.2, 287.7; 436/514, 518, 524, 528, 530, 164, 169, 805, 810, 815, 816, 901

[56] References Cited

U.S. PATENT DOCUMENTS

| | | | |
|---|---|---|---|
| 4,270,920 | 6/1981 | Kondo et al. | 435/22 |
| 4,275,149 | 6/1981 | Litman et al. | 435/7.91 |
| 4,299,916 | 11/1981 | Litman et al. | 435/805 |
| 4,959,307 | 9/1990 | Olson | 422/56 |
| 4,963,468 | 10/1990 | Olson | 422/56 |
| 5,085,987 | 2/1992 | Olson | 422/56 |
| 5,085,988 | 2/1992 | Olson | 422/56 |
| 5,238,652 | 8/1993 | Sun et al. | 422/61 |
| 5,252,496 | 10/1993 | Kang et al. | 436/529 |
| 5,424,220 | 6/1995 | Goerlach-Graw et al. | 436/568 |

FOREIGN PATENT DOCUMENTS 2239313  6/1991  United Kingdom.

OTHER PUBLICATIONS

Buechler, et al. "Simultaneous Detection of Seven Drugs of Abuse by the Triage Panel for Drugs of Abuse," *Clin. Chem.* 38(9):1678–1684 (1992).

*Primary Examiner*—Christopher L. Chin
*Attorney, Agent, or Firm*—Fredrikson & Byron, P.A.

[57] ABSTRACT

A device and related method for simultaneously performing a plurality of immunoassays to detect the presence of respective analytes in a sample. The device involves the use of a unitary bibulous material providing one or more flow paths having a common origin site and a plurality of respective reagent zones providing the reagents necessary for performing a visual read-out, competitive immunoassay for the presence of the respective analyte.

11 Claims, 1 Drawing Sheet